(12) United States Patent
Nelson et al.

(10) Patent No.: US 9,000,398 B2
(45) Date of Patent: Apr. 7, 2015

(54) SANITIZATION DEVICE FOR DENTAL ACCESSORIES

(71) Applicants: Ryan Sheldon Nelson, El Cajon, CA (US); Laura Seegobin Nelson, El Cajon, CA (US)

(72) Inventors: Ryan Sheldon Nelson, El Cajon, CA (US); Laura Seegobin Nelson, El Cajon, CA (US)

( * ) Notice: Subject to any disclaimer, the term of this patent is extended or adjusted under 35 U.S.C. 154(b) by 0 days.

(21) Appl. No.: 14/326,256

(22) Filed: Jul. 8, 2014

(65) Prior Publication Data

US 2014/0319375 A1     Oct. 30, 2014

Related U.S. Application Data

(63) Continuation-in-part of application No. 13/952,558, filed on Jul. 26, 2013, which is a continuation-in-part of application No. 13/715,953, filed on Dec. 14, 2012, now abandoned.

(51) Int. Cl.
*A61L 2/025* (2006.01)
*A61L 2/10* (2006.01)

(52) U.S. Cl.
CPC .. *A61L 2/025* (2013.01); *A61L 2/10* (2013.01)

(58) Field of Classification Search
USPC ..................................... 250/455.11
See application file for complete search history.

(56) References Cited

U.S. PATENT DOCUMENTS

| | | | |
|---|---|---|---|
| 8,246,642 B2 * | 8/2012 | Houser et al. | 606/169 |
| 8,707,504 B2 * | 4/2014 | Ryan | 15/185 |
| 8,809,807 B2 * | 8/2014 | Nelson et al. | 250/455.11 |
| 2010/0326484 A1 * | 12/2010 | Wu | 134/56 R |

* cited by examiner

*Primary Examiner* — Phillip A Johnston

(57) ABSTRACT

An external dental accessory sanitization device is configured for receiving and sanitizing a dental accessory, such as a brush, flosser, pic or other dental accessory. The sanitization device is configured to sanitize the dental accessory using one or a combination of ultraviolet light and/or sound waves. The device can be configured for sanitizing one or a plurality of dental accessories therein.

19 Claims, 13 Drawing Sheets

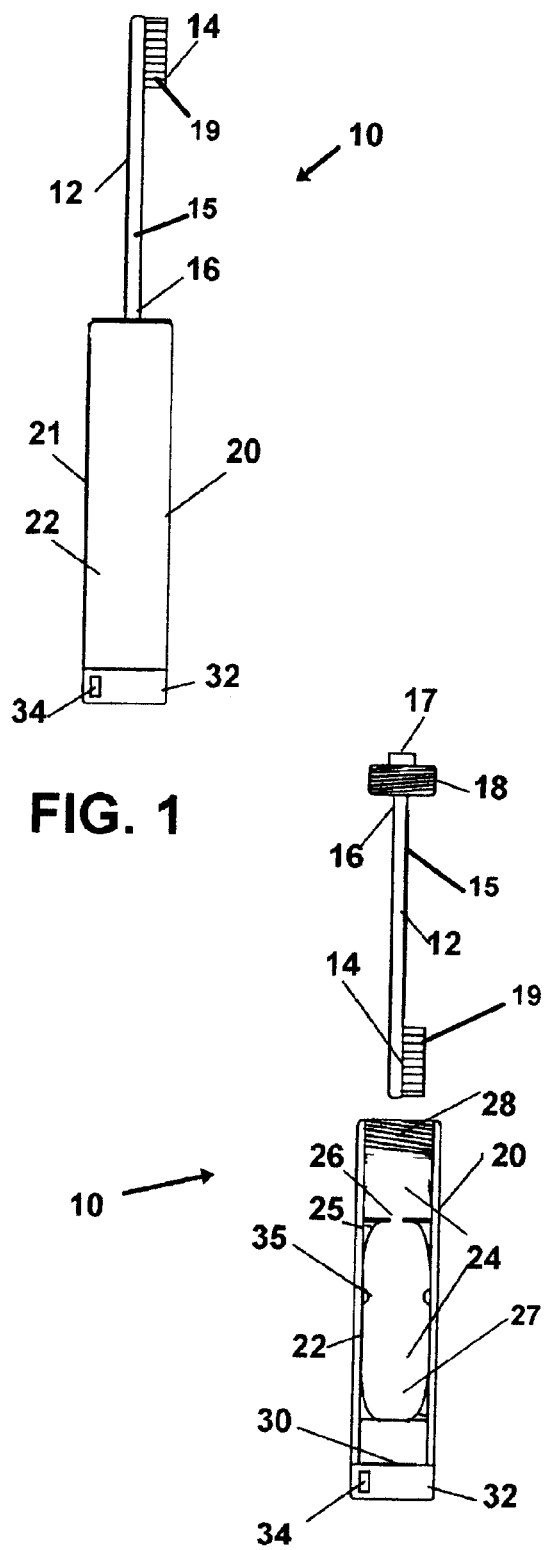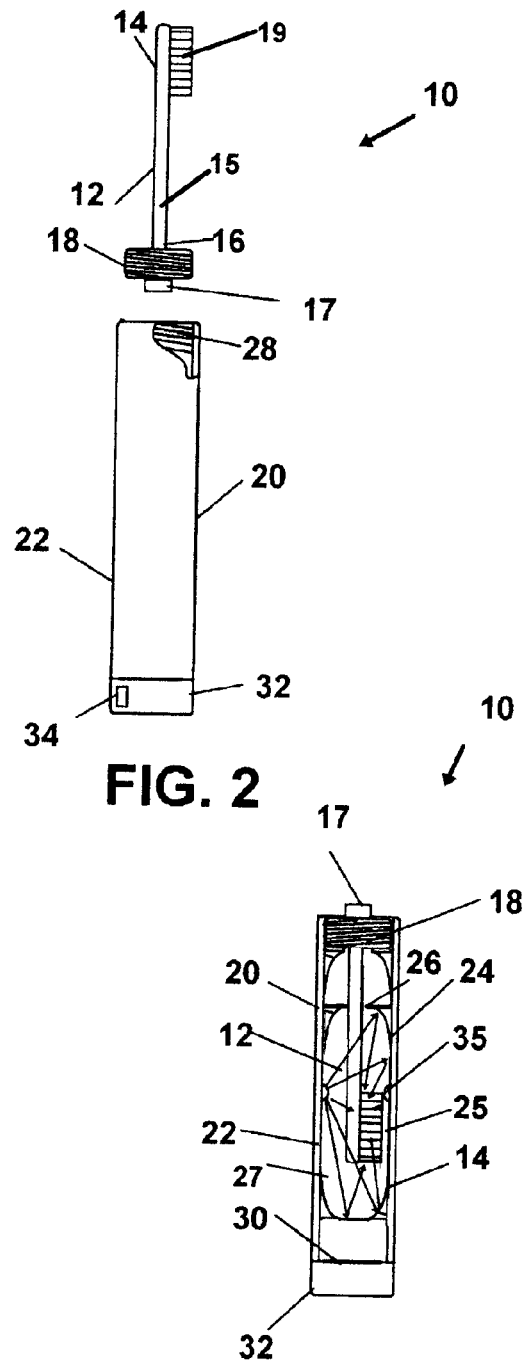

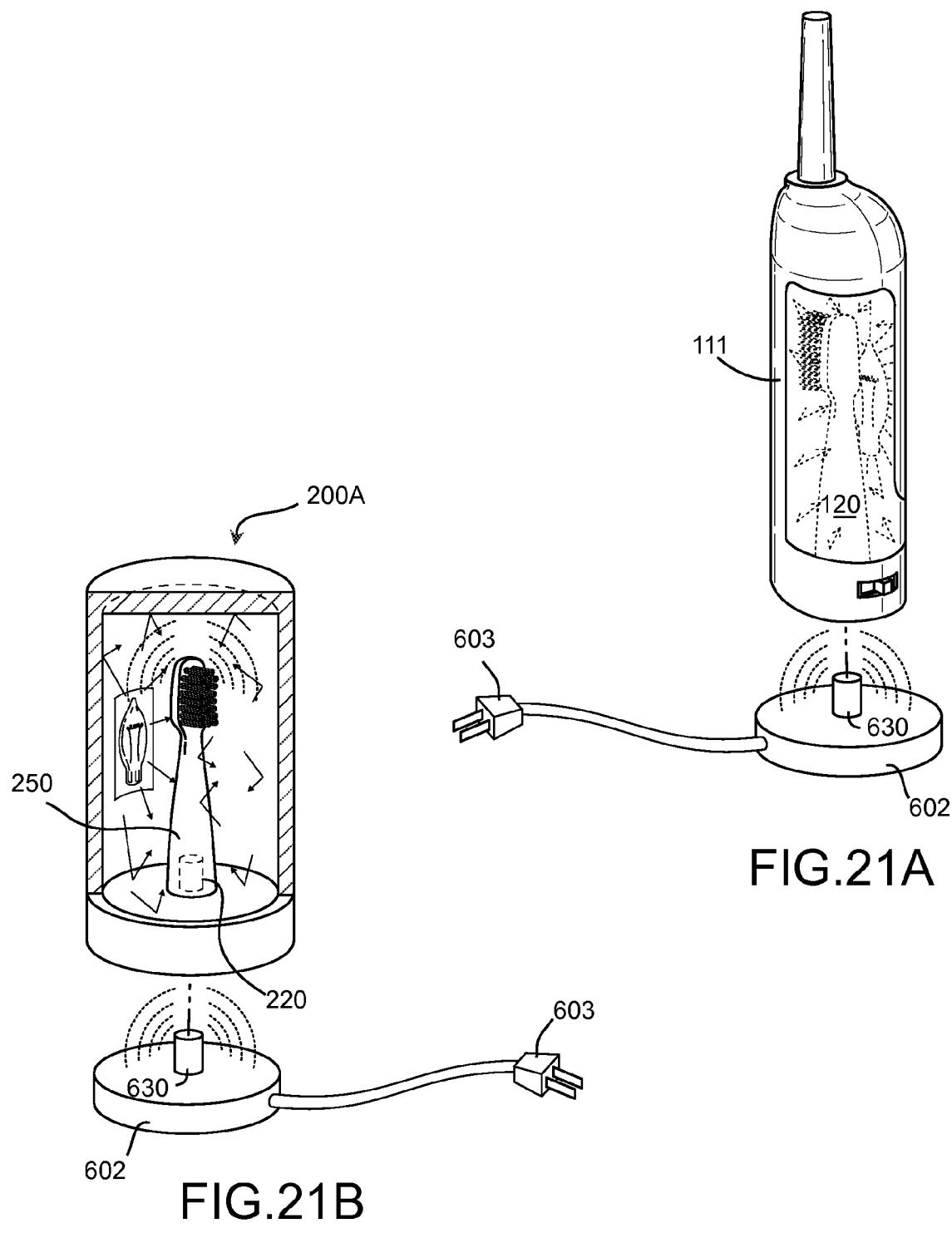

US 9,000,398 B2

SANITIZATION DEVICE FOR DENTAL ACCESSORIES

CROSS-REFERENCE TO RELATED APPLICATIONS

This application is a continuation in part (CIP) of U.S. Ser. No. 13/952,558, filed Jul. 26, 2013, and titled "DENTAL DEVICE HAVING AN INTEGRATED SANITATION CHAMBER";

which is a continuation in part (CIP) of U.S. Ser. No. 13/715,953, filed Dec. 14, 2012, and titled "SANITIZING TOOTHBRUSH";

the contents of each of which are hereby incorporated by reference.

BACKGROUND OF THE INVENTION

1. Field of the Invention

This invention relates generally to oral care devices. More particularly the invention relates to a dental sanitization device configured to employ one or a combination of ultraviolet (UV) light radiation sanitation and/or sound frequency sanitation as a means for sterilizing a dental accessory housed within a housing portion of the dental sanitization device.

2. Description of the Related Art

Toothbrushes are well known oral care devices which are recommended by dentists and oral care professional worldwide. Proper oral hygiene has been shown to dramatically reduce the occurrence of dental cavities, gingivitis, and bad breath. However, it is conventionally known through current medical research, that without proper sanitation and/or sterilization of at least the bristles of a toothbrush after use, they will contain bacteria, germs, viruses, and dirt which can contribute to the spread of disease and sickness.

As a conventional solution, many health care professionals recommend placing the toothbrush in a case or housing when not in use to reduce the chance of bacteria and germs from reaching the bristles. However, one shortfall of this approach is that the housing itself may harbor bacteria if not cleaned or sanitized properly as well. Further, wet toothbrush bristles housed in a contained area, sometimes in the dark, are a perfect breeding ground for bacteria and pathogens already present on the brush. Therefore, in order to prevent increased propagation of such pathogens while in the housing, and to actually reduce the population in the brush head, there is a need for communicating some direct sanitation and sterilization to the toothbrush itself.

Prior art has shown many other attempts to provide toothbrush sanitation and/or sterilization means through the employment of UV light irradiation. Ultraviolet germicidal irradiation (UVGI) is a known disinfection method which employs ultraviolet (UV) light at sufficiently short wavelength to kill microorganisms such as bacteria and germs. Although UVGI methods are especially preferred for sterilization means, without proper irradiation of substantially the entire surface of the majority of bristles and the brush head, colonies of bacteria and other pathogens remain which can re-propagate. Additionally, because light is directional and subject to a blockage which creates shadows, without irradiation from a majority of angles some pathogens will not be properly subjected to light sanitation. Consequently, a secondary means of sanitation of the bristles and brush head which will reach around the curves and serpentine paths of brush bristles which harbor such pathogens and either remove them or seriously reduce their population. Further, conventional toothbrushes are generally configured to be held between the thumb and fingers affording a very small area to grip or frictionally engage the handle and resulting slippage.

As a result, there is a continuing unmet need for a toothbrush sanitation device which solves these and other problems of brush sanitizers of the current state of the art. Such a device should provide a compact, storable, transportable and easy-to-use apparatus which provides illumination which strikes the brush and bristles at a maximum number of angles to provide maximum sanitizing. Such a brush optionally should provide a secondary means for sanitization which is not subject to direct line contact and which will wrap around bristles and pathways therebetween to rid or at least reduce pathogen populations. Such a toothbrush should provide for enhanced gripping by employing the housing as an enlarged grip for the handle.

The forgoing examples of related art and limitation related therewith are intended to be illustrative and not exclusive and they do not imply any limitations on the invention described and claimed herein. Various limitations of the related art will become apparent to those skilled in the art upon a reading and understanding of the specification below and the accompanying drawings.

SUMMARY OF THE INVENTION

The device herein disclosed and described provides a solution to the shortcomings in prior art and achieves the above noted goals through the provision of a toothbrush device employing a chamber having means for projecting light in a sanitizing wavelength such as ultraviolet (UV) light radiation combined with a reflective surface area of the sanitizing chamber which enhances reflection and multiplies the number of angles of communication throughout the chamber of UV light waves generated or projected into the chamber. The chamber itself is formed within the axial cavity of a housing which is removably engageable with the brush, to position the brush head within the sanitizing chamber. Of course, in other embodiments, the sanitizing chamber might also be formed to engage existing toothbrushes or other dental accessories as a means for sanitizing them. When employed with an engageable handle member, the housing may be engaged as an extension of the handle of the toothbrush and provide a larger circumference gripping area for the user to hold the handle.

In accordance with one preferred mode of the device, the housing is formed with sidewalls defining an exterior surface opposite an axially disposed sanitizing interior cavity. At least one aperture is formed in the sidewall and is positioned to be in operative communication with the interior cavity.

The interior cavity employs UV radiation means, such as one or a plurality of UV bulbs or LED's which communicate UV light. For instance ultraviolet (UV) rays with a wavelength between 100 nm and 280 nm with a particularly preferred wavelength of 254 nm will effectively kill bacteria, viruses, yeast, molds and algae which might otherwise multiply on the brush head. It is believed the UV radiation breaks through the outer membranes of such organisms, destroying or inactivating their DNA thus preventing them from reproducing. Such light sanitization safely and effectively sanitizes the brush and brush head in the axial chamber.

The light source producing light in the UV ranges of 100 nm to 260 nm communicates such into the sanitizing interior cavity which is preferably lined circumferentially with a reflective angled curvilinear surface. This angled circumferentially disposed surface causes reflections and re-reflection of communicated UV light. Thus directly radiated and reflectively radiated light rays from the UV source impact the brush head and bristles at many different angles concurrently, to remove pathogens which otherwise would thrive in hidden areas of the bristles.

The housing additionally includes means for powering the UV radiation means, such as a rechargeable battery, or other suitable means for storage of electrical power sufficient to power the UV light or LED. Additionally preferred is a pulsing of the UV light from the irradiation source from a lower energy radiation to a higher energy or much brighter radiation of light, to generate sequential higher energy pulses of UV light which will reflect into more hidden areas of the brush head from subsequent reflecting from the reflective angled surfacing.

Optionally, but preferable as a secondary sanitation means, sound frequency sanitizing may be employed concurrently with the light sanitization. Such may be accomplished by the communication of sound waves into the sanitizing chamber from a means for sound generation in the proper frequencies. For instance, Ultrasonic waves ranging from 20 to 100 kHz in frequency have been successfully used as a surface cleaning technique in the medical and precision processing industries for a number of years. Various pathogens suffer damage and may be removed at other frequencies which may be ascertained from literature on the subject however the current favored mode is noted above.

Means for generation and communication of sonic waves into the sanitization chamber to provide the sound frequency sanitization, would be a frequency wave tone generator which would receive power from onboard battery power or other sound frequency generators which will produce sound in the above noted frequency ranges. A microchip controller may be employed to sequentially move the sound generation to the individual frequencies adapted to kill the desired pathogens for periods of time before moving to other individual frequencies.

Although certain wavelength and frequency ranges are herein provided for illustrating effective sanitization by means of light and sound, it should be understood that the dental device can be configured to emit any light wavelength, or any sound frequency, with minor variation in component selection, to accomplish the objective of sanitizing the dental accessory or instrument. Accordingly, the scope of the invention is not to be limited with respect to the above illustrative examples.

In one as-used mode for sanitization, the toothbrush portion, if employed in combination, is positionable in an engagement to the housing, such that the housing is employed as a handle for operating the toothbrush in a conventional manner. In a second as used mode or sanitization mode, the toothbrush portion is reversible in its engagement with the housing, such that the toothbrush head having bristles thereon is positionable in registered engagement within the interior cavity of the housing, and adjacent the reflective surfaces and in communication with the UV radiation and/or sound frequency sanitization means communicated therein. Activation of the UV light source and/or sound frequency generation source can be provided by an operable switch on the exterior of the housing. The switch may be on a timer as needed for conserving battery power.

In an alternative embodiment, a sanitation device for sterilization of one or more dental accessories therein is provided. The sanitation device comprises: a base having one or more attachment members, each of the attachment members being configured to engage with one of the dental accessories for maintaining an orientation thereof about the base; a cover having a top portion and one or more side walls extending therefrom, wherein the side walls are configured to engage a periphery of the base and form an engagement therebetween; the cover when coupled to the base in a closed-position forms an interior volume therebetween, the interior volume defining a sanitation chamber; and the device further comprising one or more of: at least one ultraviolet light emitting source disposed within the sanitation chamber; or an ultrasonic sound frequency generator configured to communicate ultrasonic energy within the sanitation chamber.

With respect to the above description, before explaining at least one preferred embodiment of the herein disclosed invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is housing may readily be utilized as a basis for designing of other structures, methods and systems for carrying out the several purposes of the present disclosed device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising".

Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The objects features, and advantages of the inventive embodiments, as well as the advantages thereof over existing prior art, which will become apparent from the description to follow, are accomplished by the improvements described in this specification and hereinafter described in the following detailed description which fully discloses the invention, but should not be considered as placing limitations thereon.

BRIEF DESCRIPTION OF THE DRAWINGS

The accompanying drawings, which are incorporated herein and form a part of the specification, illustrate some, but not the only or exclusive, examples of embodiments and/or features. It is intended that the embodiments and figures disclosed herein are to be considered illustrative rather than limiting. In the drawings:

FIG. 1 shows a view of the device comprising a toothbrush portion and a housing portion employing UV radiation means, in a first as used mode, with the brush positioned in an engagement with the housing such that the housing is employed as a handle affording a larger circumference for an enhanced grip during conventional operation of the brush.

FIG. 2 shows the toothbrush portion disengaged from the housing.

FIG. 3 shows the toothbrush portion being reversed in its position relative the housing.

FIG. 4 shows the device in another preferred as used sanitizing mode, wherein the toothbrush portion has been reversed in its engagement with the housing, such that the toothbrush head is communicated into the sanitizing cavity of the housing having surrounding mirrored or reflective walls for light from a UV radiation means and/or sound frequency sanitization from a means for sound generation at the appropriate frequencies noted.

FIGS. 21(A-B) show a base configured to engage a toothbrush device with built-in sanitization chamber, or an external device; the base is configured to communicate ultrasonic frequency to the attached device.

DETAILED DESCRIPTION OF THE PREFERRED EMBODIMENTS

Figure 5:
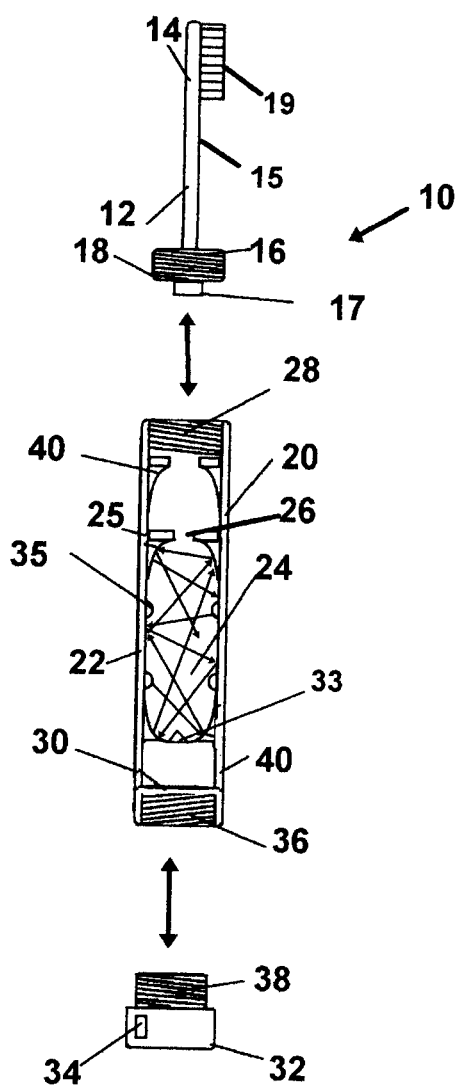
FIG. 5 shows another preferred mode of the device being a three-piece mode having a housing, and removably engageable toothbrush portion and battery. It should be noted that the housing and power source may be employed separately with a non-provided toothbrush in another mode of the device.

In this description, the directional prepositions of up, upwardly, down, downwardly, front, back, top, upper, bottom, lower, left, right and other such terms refer to the device as it is oriented and appears in the drawings and are used for convenience only; they are not intended to be limiting or to imply that the device has to be used or positioned in any particular orientation.

Now referring to drawings in FIGS. 1-5, wherein similar components are identified by like reference numerals, there is seen in FIG. 1 a view of the device 10 in a first as used mode with the toothbrush portion 12 provided. The device 10 includes a toothbrush portion 12 and a housing 20. The toothbrush portion 12 includes an elongated member forming a handle 15 having a head end 14 having bristles 19, all combining to yield a toothbrush.

The handle 15 has an engagement end 16, including means for removable engagement of the handle 15 to extend axially from an engagement to the housing 20, such as cooperative engagement components positioned on each of the housing 20 and handle 15, such as mating threads 18, or a frictional engagement, or other means for engagement of the distal end of the handle 15, to the housing 20, to allow the housing 20 to function as an extension of the handle 15 and provide and enlarged grip circumference for the handle 15. So engaged the user can more easily hold the device 10 assembled with the toothbrush 12 extending axially from one end of the housing 20 which is gripped in the user's hand.

The housing 20 has a substantially cylindrical elongated body 21 having an axially oriented interior cavity 24 defined by an interior surface of one or a plurality of sidewalls 22. The interior cavity 24 has a sanitizing chamber 27 formed by the reflective or mirrored interior sidewall 22 terminating at an end wall 30, and at an opening 26 providing a communication from exterior to the housing 20 into the sanitizing chamber 27. It is preferred that the opening have a circumference just slightly larger than a circumference of the handle 15 to allow passage of the head therethrough and to thereby minimize the escape of any UV light and/or sound from the sanitizing chamber 27.

Additionally, there is included a means for UV radiation positioned to communicate UV light into sanitizing chamber 27 portion of the cavity 24, such as a plurality of UV lights 35 provided by bulbs or LED's generating UV light in the ranges between 100-280 nm. As can be seen, the curved reflective surface along the length of the sanitizing chamber 27 and at both ends of the sanitizing chamber 27 combined with minimizing loss through provision of an opening just slightly larger than the handle 15, provides means for vectoring the light generated by the means for UV illumination such as the LED or UV light 35, toward the brush head at an infinite number of angles depending on the reflection from multiple surfaces. Further the opening 26 being sized just larger than the circumference of the handle 15 minimizes loss.

Means for electrical power for the means for UV radiation and/or a sound frequency generator, 33 may be provided by a rechargeable battery 32 operatively engaged with the housing 20, and electrically engaged to the means for UV illumination such as UV lights 35 and/or wave tone generator 33 which provides a means for ultrasonic or sound sterilization.

Means for removable engagement of the toothbrush portion 12 to the housing 20 is provided by a cooperative fastening components on each of the housing 20 and the handle 15 such as a threaded engagement of the engagement handle 15 to an interior threaded portion 28 of the housing 20 at or near the open end 26 of the housing 20. So engaged, the handle 15 extends axially from the housing 20 which has the larger circumference to provide and enhanced gripping area for the hand of the user. Although threaded engagement is one preferred means of removable engagement, other means for removable engagement may be employed and are anticipated, for example, the removable engagement means can be snap fits, frictional engagement, a bayonet style engagement of mating components, or other suitable means.

As noted, in a first depicted as used mode in FIG. 1, the toothbrush 12 is provided for use in combination with a housing 20 and the toothbrush portion 12 may be engaged with the housing 20 such that the housing 20 is employable as an extension of the handle 15, with an enlarged circumferential grip, for conventional operation of the toothbrush 12. As noted earlier however, the housing 20 can be manufactured and employed as a stand-alone device, configured to engage with and sanitize other toothbrushes already owned or manufactured through employment of the novel sanitizing chamber 27 and combination of UV and sound frequency sanitization.

In yet another preferred as used mode in FIG. 3 and FIG. 4, the toothbrush 12 is reversible in its engagement with the housing 20 as shown. As can be seen, once disengaged from the housing 20 as shown in FIG. 2, the toothbrush 12 is reversible such that the head end 14 of the toothbrush 12 can be communicated into the central area of the cavity employed as the sanitizing chamber 27. As shown, so inserted light and sound if employed, is reflected at an infinite number of multiple angles to allow penetration to all areas of the bristles as well as the circumferentially around the inserted toothbrush 12.

A switch 34 can be provided to allow the user to control electrical power to the UV lights 35 for UVGI sanitation and/or disinfection of the toothbrush 12 or to the sound frequency generator 33 for sound sanitation. The switch may allow for independent or concurrent use of UV and/or sound sanitation at the noted frequencies. As noted and preferred, sanitation is significantly enhanced by coating or otherwise forming the interior surface 25 of the sanitizing chamber 27 within the interior cavity, with a reflective material and angular circumferential sections, reflect the UV light within the sanitizing chamber 27 for improved sterilization. The curved ends and central areas of the reflective portion of the sanitizing chamber 27 also serve to reflect sound waves at an ultimate the number of different angles depending on number and angle of each reflection. Additionally, a tab 17 engaged to the toothbrush 12 portion of the device 10, allows the user to grasp the toothbrush 12 and rotate it out of its engagement the housing when in the second as used mode or sanitizing position.

FIG. 5 shows yet another preferred mode of the device 10, similar to the previous mode however having a removably engageable battery component 32. In this mode the battery component 32 can more be seen as easily removed and so as to be charged on a charger docking component (not shown) for an efficient recharge as needed. Currently, means for removable engagement are provided by a threaded distal end portion 36 of the housing 20 and complimentary threaded portion 38 on the battery component 32. However, it is noted that other means for removable engagement such as a bayonet mount, or frictional engagement, or other engagement means as would occur to those skilled in the art may be employed, and which are anticipated.

In an exceptionally preferred feature of the current mode, is the employment of one or a plurality of circumferentially reflecting curved mirror 40 portions of the reflective surface positioned within sanitizing chamber 27 of the housing 20. The mirror 40 portions are substantially concave and curve around a 90 degree angle to provide a means for communicating the light emitted from the UV lights 35, and the sound from the sound frequency generator 33, to all interior surface areas 25 within the sanitizing chamber 27, due to the reflective quality of such, further enhancing UV sterilization. In addition, the mirror 40 portions can be formed of suitable material to provide enhanced means for sound frequency reflection, such as a hardened polymer, for reflecting the emitted sound frequencies from the frequency wave tone generator or sound frequency generator 33 to all interior surface areas 25 within the sanitizing chamber 27.

In another embodiment, a dental device comprises a handle portion and an accessory portion. The handle portion forms a housing with an interior cavity and an external gripping surface. The interior cavity is sealed with a hinged door forming at least a portion of the housing wall, the hinged door configured to open for providing access to within the interior cavity, and further configured to close during a sanitation cycle. The interior cavity forms a sanitation chamber by way of a reflective interior wall and at least one of an ultraviolet light source or a sound wave transducer configured to sanitize one or more objects or dental accessories within an interior volume thereof. In this regard, the dental accessory may comprise a brush, flosser, pic, massager, tongue cleaner, or other accessory, and is configured for removable attachment with the device. The dental accessory is further configured with a size sufficient to permit containment of the accessory within the sanitation chamber for undergoing one or more sanitation cycles therein.

Figure 6:
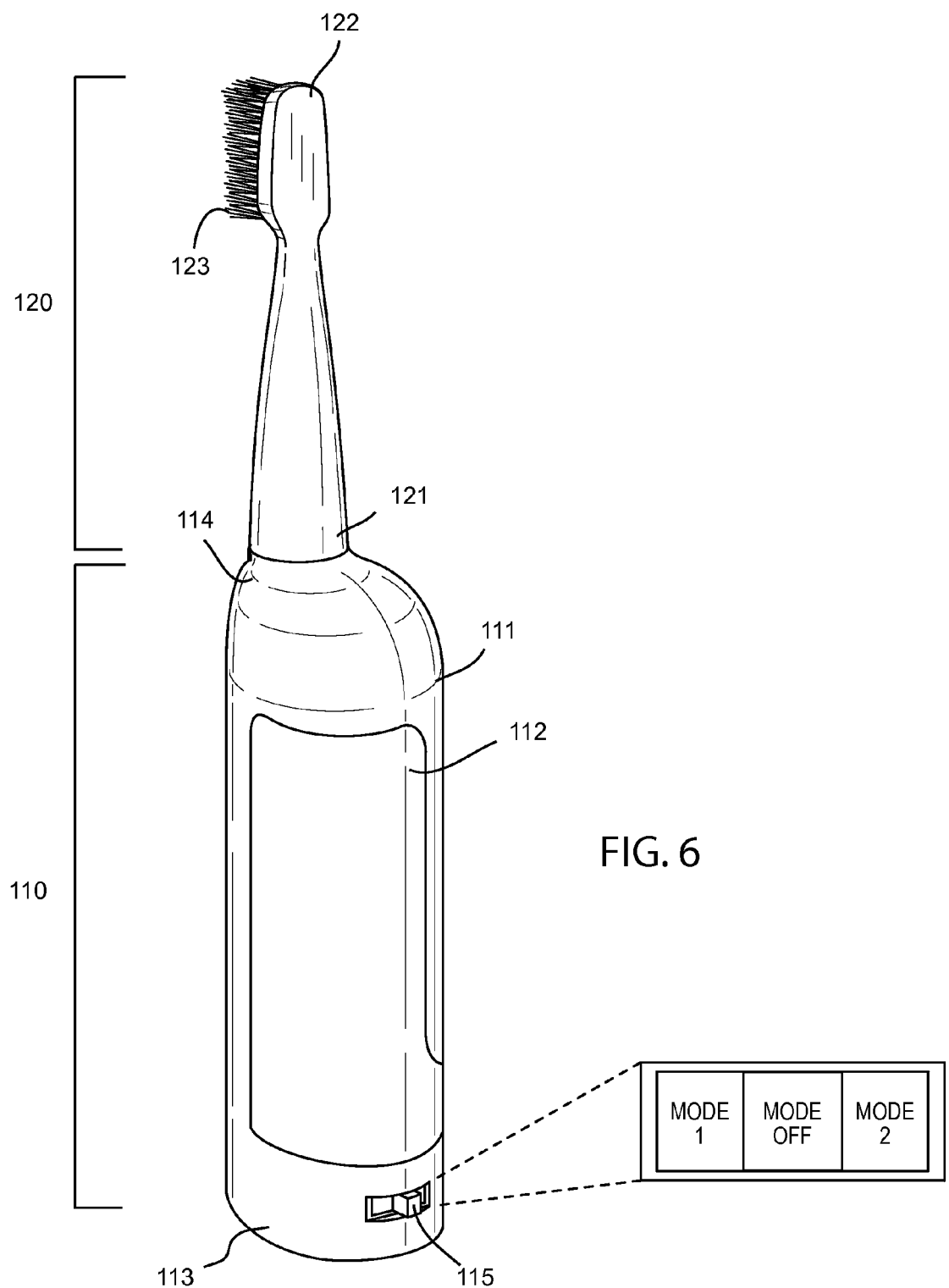
FIG. 6 shows the device in accordance with another embodiment, wherein the device comprises a device handle forming housing with a hollowed cavity wherein an interior portion thereof is configured with a sanitation chamber for sanitizing one or more dental accessories.

Turning now to FIG. 6, a dental device comprises a handle portion 110 and an accessory portion (116, FIG. 7) extending outwardly from the handle portion 110. A brush accessory 120 is being shown and is removably attached to the accessory portion 116 of the device; however, any dental accessory may be attached in accordance with this embodiment and a brush accessory is shown for purposes of illustration only. The brush accessory 120 extends from a bottom end 121 to a top end 122 thereof, and a plurality of bristles 123 extend laterally from the top end of the brush accessory 120. The handle portion 110 comprises housing 111 formed by a circumferential wall extending along a length of the handle portion from a bottom end 113 to a top end 114 thereof. The housing 111 further defines an exterior gripping surface configured to enhance a user's grip of the device, and an interior cavity (131, FIG. 7) within the housing forming a sanitation chamber for sanitation of one or more objects therein. Here, the hinged access door 112 is being shown in a closed state, thereby sealing the interior volume of the sanitation chamber. A switch 115 or button, referred to as a "sanitation trigger", is disposed about the housing and provides a mechanism for operating the sanitation chamber function. The sanitation trigger may be configured to select up to any of a "first mode", a "second mode", or "OFF". The first mode may be associated with a first time-duration, a first light intensity, or other pre-determined setting. The second mode may be associated with a second time-duration that is distinct from the first time-duration, a second light intensity, or another pre-determined setting. In this regard, the dental device is configured for removable attachment of one or more dental accessories, and sanitation of the one or more dental accessories within the sanitation chamber. The chamber door 112 provides improved access to internally housed objects.

Figure 7:
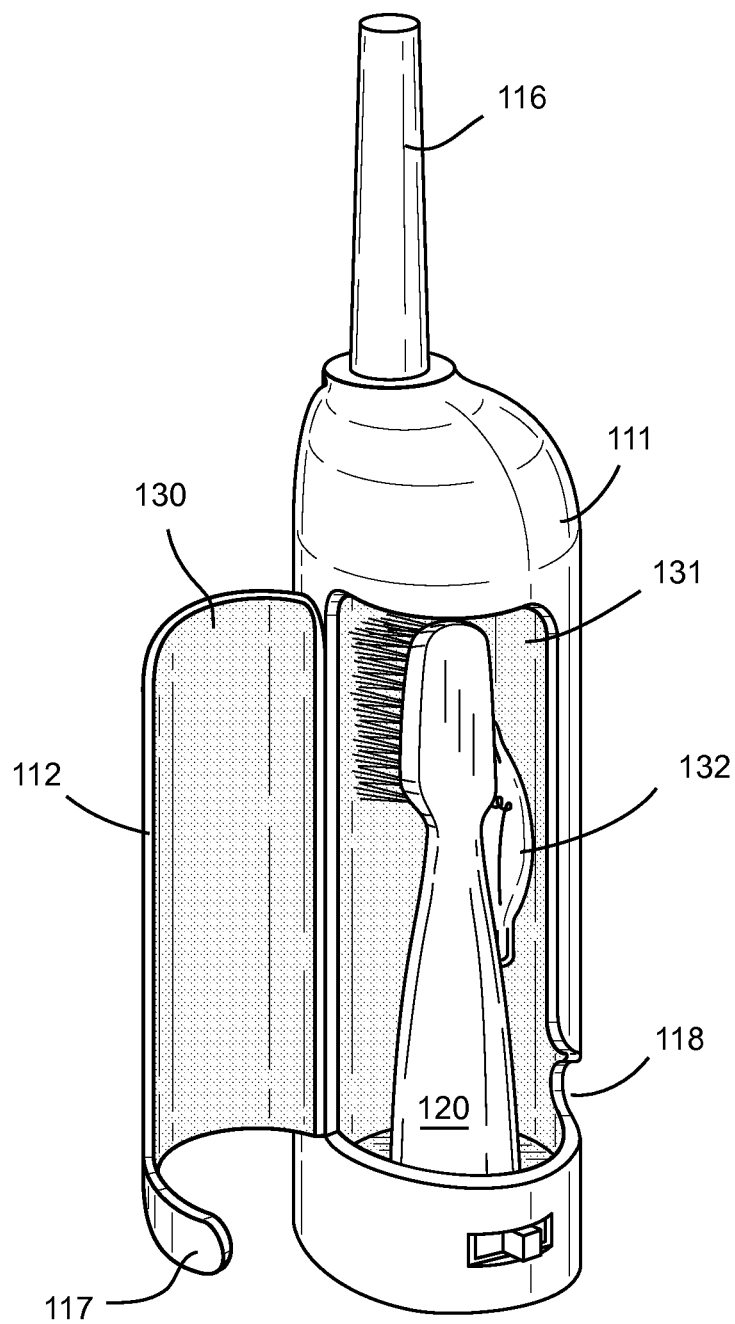
FIG. 7 shows the device of FIG. 6 with a cavity door being opened for permitting access to the interior cavity of the sanitation chamber.

FIG. 7 shows the dental device of FIG. 6 with the hinged chamber door 112 configured in an open state. The hinged door 112 is configured to close about the housing 111 with a tab 117 extending from the door being configured to nest within a notch 118 of the housing for providing a flush surface when in the closed state. The sanitation chamber 131 is shown with the brush accessory 120 disposed therein. The sanitation chamber comprises a reflective interior wall 130 disposed on the interior surface of the hinged door 112 and about a majority of the interior surface of the sanitation chamber 131. The reflective interior wall may comprise Mylar sheets, a metallic foil, a reflective coating, or other reflective material sufficient to reflect light about an interior volume of the sanitation chamber otherwise referred to as the interior cavity within the housing. The sanitation chamber further comprises at least one ultraviolet light emitting source 132, such as an ultraviolet light bulb, light emitting diode, or other light emitting device configured to emit ultraviolet light within the sanitation chamber during a sanitation cycle. The accessory portion 116 of the device is more clearly shown, and is configured to receive and engage an accessory such as a brush, flosser, tongue cleaner, pic, or other dental accessory.

Figure 8:
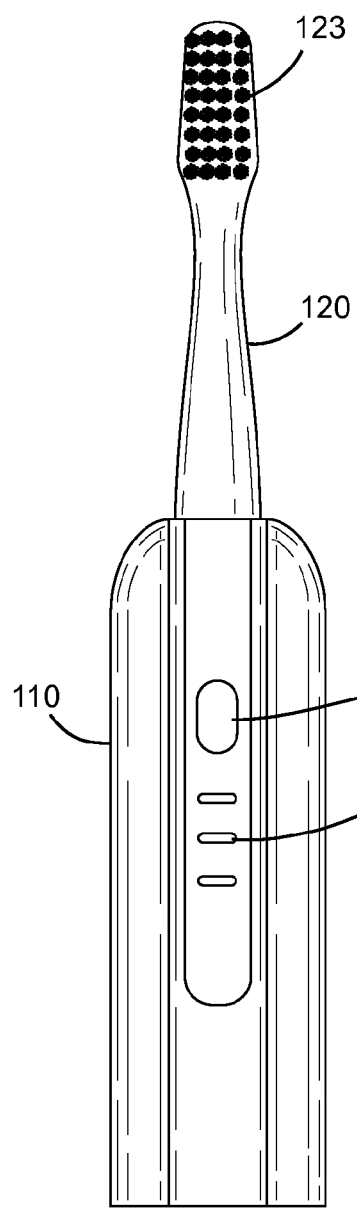
FIG. 8 shows a front view of the device according to the embodiment of FIGS. 6-7.

FIG. 8 shows the dental device of FIGS. 6-7 in accordance with a front view. The dental device may comprise one or more buttons 140 or switches, collectively the "accessory trigger", for operating the dental accessory, or the brush accessory as shown. Additionally, one or more indicator lights 141 may be disposed on the handle portion 110 and adjacent to the buttons or switches for communicating a present mode or setting of the accessory during an operation thereof. The brush accessory 120 is shown having a plurality of bristles 123 disposed at the top end and extending laterally.

Figure 9:
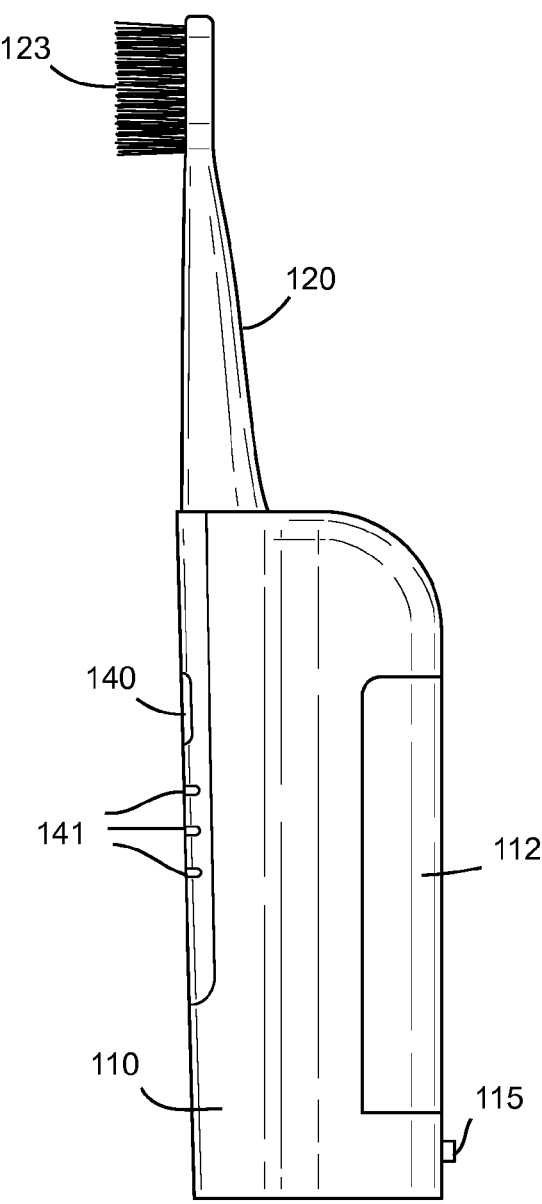
FIG. 9 shows a side view of the device according to the embodiment of FIGS. 6-8.

FIG. 9 shows a side view of the dental device of FIGS. 6-8. The hinged door 112 may be configured near a rear side of the housing as shown. Alternatively, the hinged door can be positioned on a side of the housing (not shown). It has been determined that the accessory trigger 140 for operating the function of the accessory 120 may preferably be disposed on a side opposite of the sanitation trigger 115 for operating the sanitation cycles of the sanitation chamber. Here, the accessory trigger 140 is shown positioned near a front surface of the housing, whereas the sanitation trigger 115 is shown being positioned near a rear surface of the housing opposite of the front surface. Such a physical separation of the individual triggers tends to prevent unintended use of each functional aspect of the device, thus preventing undesired or wasted energy from unwanted operations of the accessory or sanitation chamber. It should be noted that although shown in accordance with this preferred architecture, the triggers may be positioned anywhere on the device.

Figure 10:
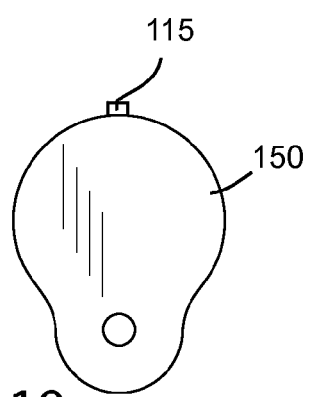
FIG. 10 shows a bottom view of the device according to the embodiment of FIGS. 6-9.

FIG. 10 shows a bottom view of the dental device of FIGS. 6-9. Although an hourglass section is shown, the body portion may comprise a circular, triangular, oblong, or other shape as may be desired by a user for gripping and ergonomic performance. A bottom surface 150 may be configured to engage a charging dock with an electronic port disposed thereon. The sanitation trigger 115 is shown extending from a rear side of the device.

Figure 11:
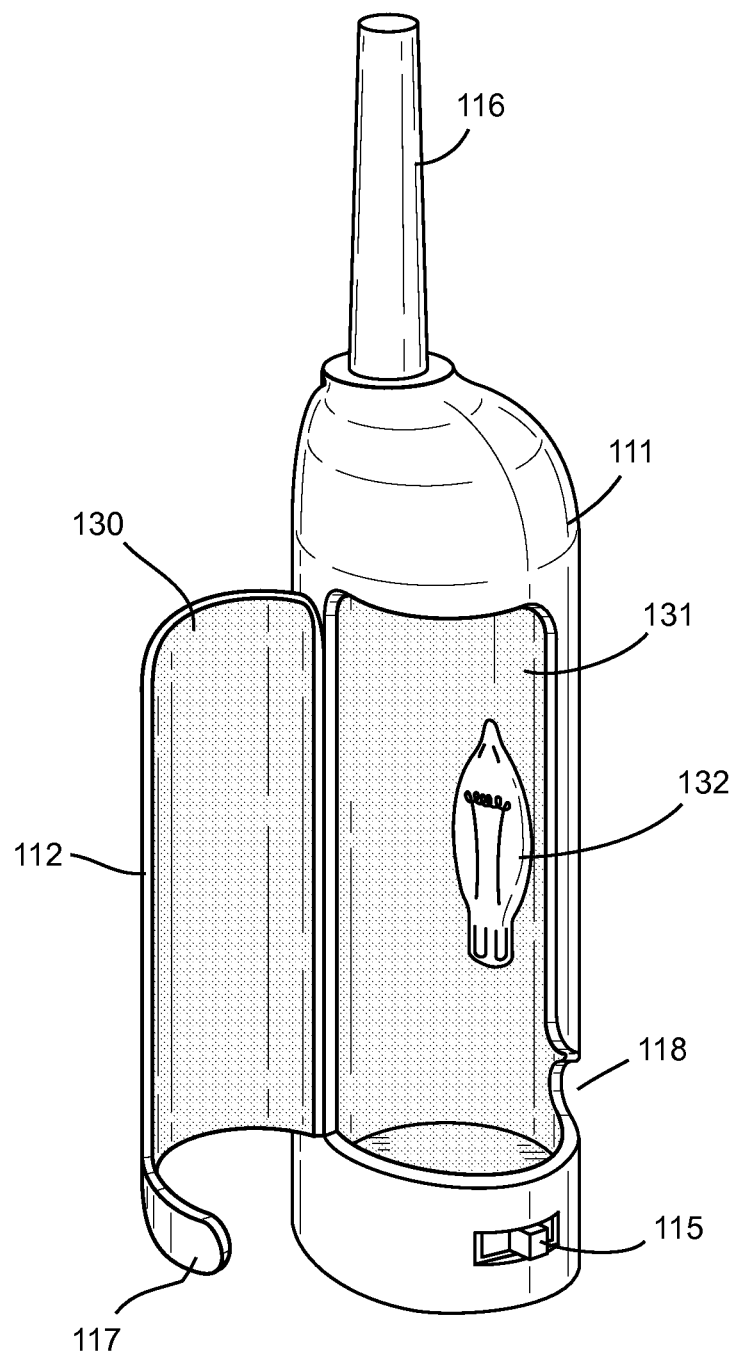
FIG. 11 further shows the interior cavity of the sanitation chamber of the device in accordance with the embodiment of FIGS. 6-10, the interior cavity having a reflective surface disposed on an interior wall thereof, and a light bulb positioned within the interior cavity for providing an amount and frequency of light sufficient for sanitization therein.

FIG. 11 further illustrates the sanitation chamber 131 within the dental device housing 111 in accordance with the embodiment of FIGS. 6-10. The sanitation chamber 131 comprises at least one ultraviolet light source 132 configured to emit ultraviolet light within the sanitation chamber, and a reflective inner wall surface 130 covering the inner door surface and the inner sanitation chamber wall surface. The hinged chamber door 112 is configured to hingedly open about a length of the housing for providing access to an interior volume of the sanitation chamber 131. The door also closes to a flush position for sealing the interior volume of the sanitation chamber. A clasp, friction fit, or other component may be provided for securing the hinged door in a closed state (not shown). The hinged chamber door may further comprise a tab 117 for engaging and opening the chamber door 112 from the closed state to an open state. The tab 117 of the hinged door is configured to nest within the housing notch 118 to form a flush surface for smooth gripping of the handle portion when in a closed state. A receptacle or similar component may be provided within a bottom portion of the sanitation chamber for receiving one or more objects or accessories.

Figure 12:
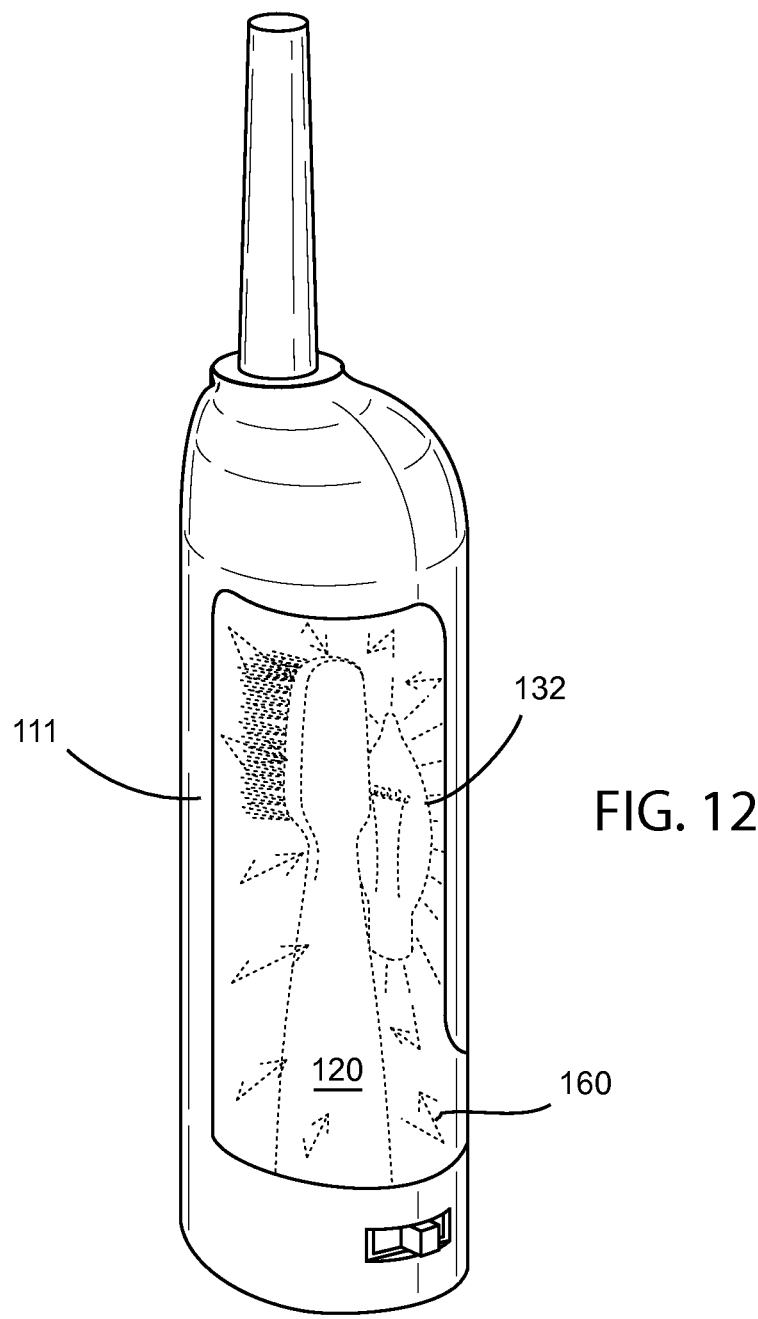
FIG. 12 further shows a sanitization cycle of the device in accordance with the embodiment of FIGS. 6-11, the sanitization cycle comprising emission of ultraviolet light within the sanitation chamber, the light being reflected about the interior wall surface, thereby sanitizing any dental accessories contained therein.

FIG. 12 illustrates the dental device in accordance with the embodiment of FIGS. 6-11. The brush accessory 120 is positioned within the sanitation chamber of the housing 111, the chamber door is in a closed state, and an amount of ultraviolet light 160 is being emitted from the ultraviolet source 132 and reflected about the interior reflective wall. During a sanitation cycle, bacteria and other pathogens are neutralized and the dental accessory within the chamber during the sanitation cycle is sanitized for future use.

The dental device may be powered by a single power source, such as one or more disposable batteries, one or more rechargeable batteries, or other commercially available power source. The dental device may be configured to recharge within a charging dock, or become engaged with a power cord, solar charged or other charging mechanism when embodied in a rechargeable form.

In other embodiments, a sanitation chamber is configured to removably attach with an existing toothbrush or other dental instrument. The sanitation chamber comprises a housing configured to receive at least a portion of the dental instrument therein. The housing comprises an aperture for receiving the at least a portion of a dental instrument, an interior sanitation chamber volume, an interior wall surface configured to reflect light within the sanitation chamber volume, and a sanitizing light emitting source such as a UV light emitting diode or other light source. In this regard, the sanitation chamber is configured to receive at least a portion of a dental instrument, introduce a sanitizing exposure of light within the sanitation chamber and reflect the light about the sanitation chamber volume for sanitizing bacteria and other pathogens within the sanitation chamber.

External Sanitization Device for Dental Accessories

In an alternative embodiment, an external sanitization device for sterilization of one or more dental accessories therein is provided. The sanitization device comprises: a base having one or more attachment members, each of the attachment members being configured to engage with one of the dental accessories for maintaining an orientation thereof about the base; a cover having a top portion and one or more side walls extending therefrom, wherein the side walls are configured to engage a periphery of the base and form an engagement therebetween; the cover when coupled to the base in a closed-position forms an interior volume therebetween, the interior volume defining a sanitation chamber; and the device further comprising one or more of: at least one ultraviolet light emitting source disposed within the sanitation chamber; or an ultrasonic sound frequency generator configured to communicate ultrasonic energy within the sanitation chamber.

Similar to the embodiments disclosed above, the external sanitization device may utilize ultraviolet light emitted from an ultraviolet light emitting source, such as UV light bulb or similar component.

Moreover, the external sanitization device herein may utilize an ultrasonic sound frequency generator, such as an ultrasonic sound transducer, or oscillating motor, to generate ultrasonic sound waves at frequencies for killing microbes and other infectious agents. An example of a sound transducer may include an ultrasonic piezo transducer. It has been shown that certain ultrasonic frequencies, such as those within the range of 20 KHz and 100 KHz, are effective at killing bacteria and pathogens. However, any sound frequency that either kills pathogens, viruses or bacteria, or assists in a sterilization process, may be implemented in a similar fashion.

Each of the general features of the above embodiments may be integrated with an external device for accomplishing the goal of sanitizing dental accessories using one or more of UV radiation and ultrasonic energy. In this regard, each of the UV radiation and ultrasonic energy, or a combination thereof, is capable of sterilizing the dental accessory by killing bacteria and pathogens as described above.

Now referring to FIGS. 13-20 and the following descriptions, an external sanitization device for sterilization of one or more dental accessories in accordance with several embodiments is herein described and illustrated.

Figure 13:
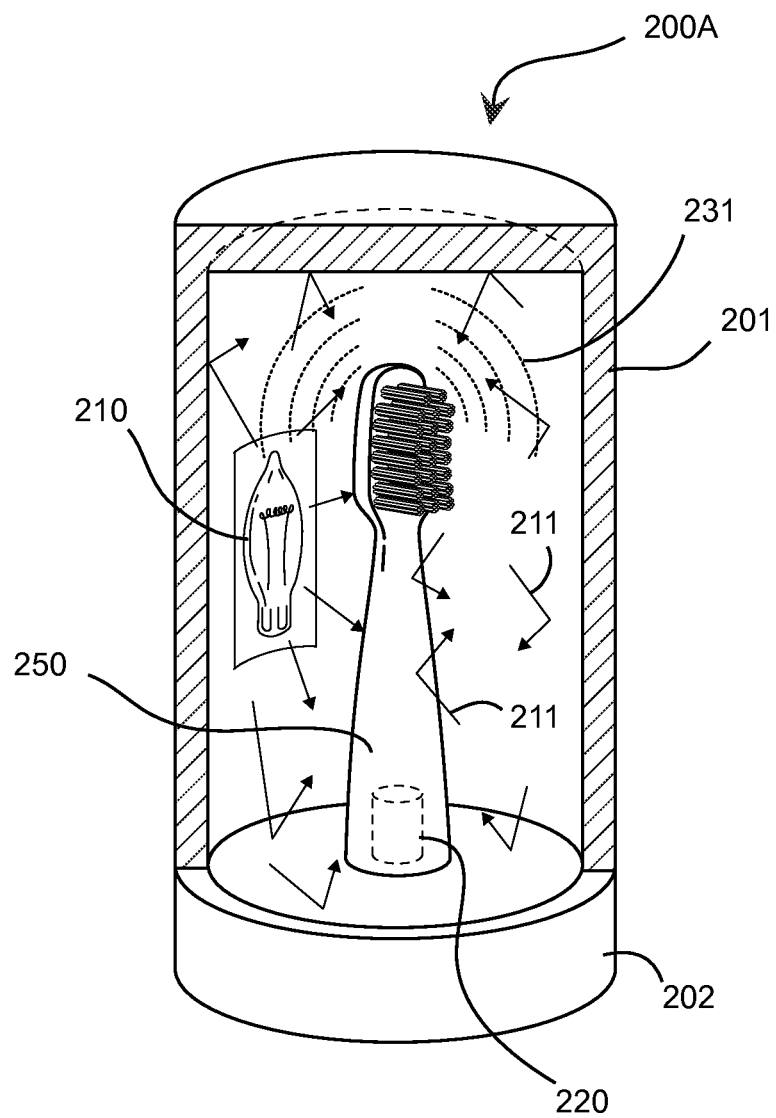
FIG. 13 shows an external sanitization device configured to sanitize a dental accessory using a combination of ultraviolet light and ultrasonic energy; the device is configured for a single dental accessory and is generally configured for personal use or as a travel product.

FIG. 13 shows an external sanitization device configured to sanitize a dental accessory using a combination of ultraviolet light and ultrasonic energy; the device is configured for a single dental accessory and is generally configured for personal use or as a travel product. The sanitization device 200A comprises a base 202 and a cover 201. The cover has a top portion and a cylindrical side wall extending therefrom toward a rim of the cover, the rim of the cover is configured to engage with a periphery of base 202 forming a seal between the cover and the periphery of the base. A hollow volume between the cover and the base when in a closed position forms a sanitation chamber. A dental accessory, such as a toothbrush accessory 250, is shown mated with an attachment member. In this regard, the dental accessory may comprise a notch 220 or other means for engaging the accessory with the attachment member. When the accessory is engaged with the attachment member, the accessory can be configured for orientation about the base of the device. For example, the accessory can be oriented such that a head portion is facing the ultraviolet light emitting source of the device for sanitizing the useful portion of the accessory.

The attachment member can comprise a peg or volumetrically shaped form configured to engage with the notch of the accessory. The attachment member can be coupled to the ultrasonic sound frequency generator such that ultrasonic energy 231 is communicated through the dental accessory from a body portion thereof to the head portion, such as the bristles of a toothbrush accessory 250. Although a peg is shown and described, it will be recognized by those with skill in the art that alternatives, such as a clasp, magnetic attachment means, and other implementations can be incorporated without departing from the scope of the invention as claimed.

In addition, the device of FIG. 13 shows an ultraviolet light emitting source 210 configured to communicate ultraviolet light 211 within the sanitation chamber of the device. Thus, the dental accessory can be sterilized by a combination of ultraviolet light and ultrasonic energy.

The cover 201 is shown comprising a reflective surface for reflecting the ultraviolet light within the sanitation chamber. In practice, however, the device can alternatively comprise a clear, transparent, and non-reflective cover.

Figure 14:
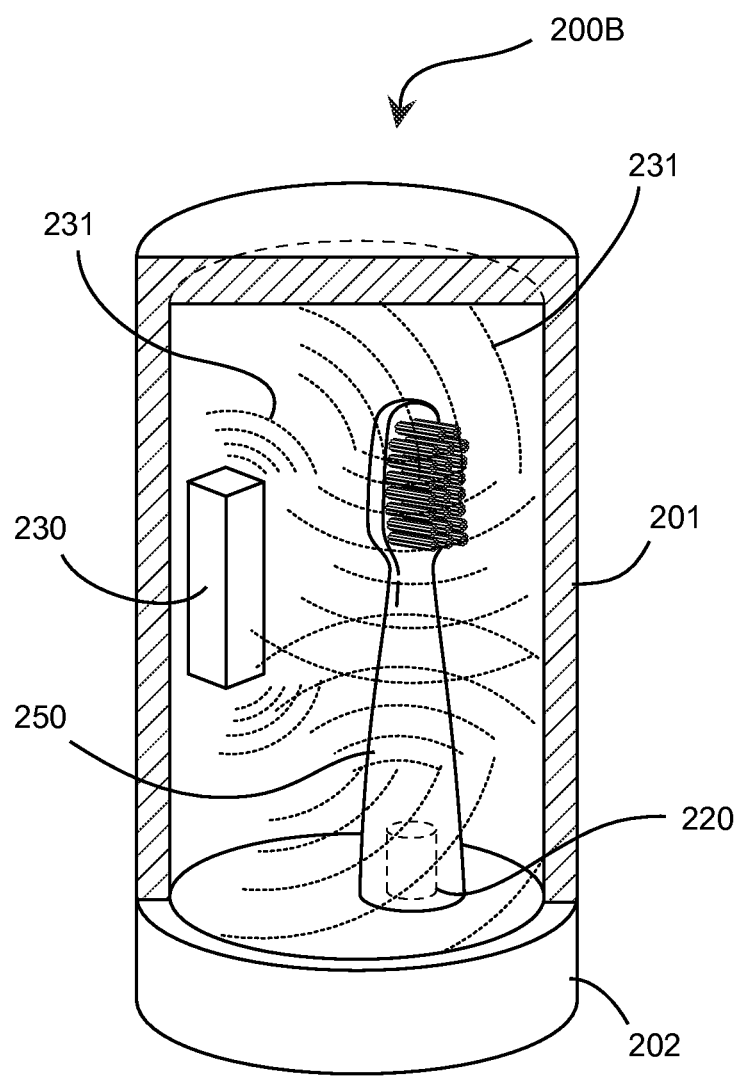
FIG. 14 shows an alternative embodiment to that shown in FIG. 13, wherein the sanitization device is configured to sterilize a dental accessory using only ultrasonic energy.

FIG. 14 shows an alternative embodiment to that shown in FIG. 13, wherein the sanitization device 200B is configured to sterilize a dental accessory using only ultrasonic energy 231, or sound waves. Although the ultrasonic sound frequency generator is shown positioned about the cover 201, it should be noted that the generator can be alternatively integrated within the base 202. Moreover, the ultrasonic sound frequency generator can be coupled to the attachment member for directly communicating ultrasonic energy to the head of an engaged dental accessory.

Figure 15:
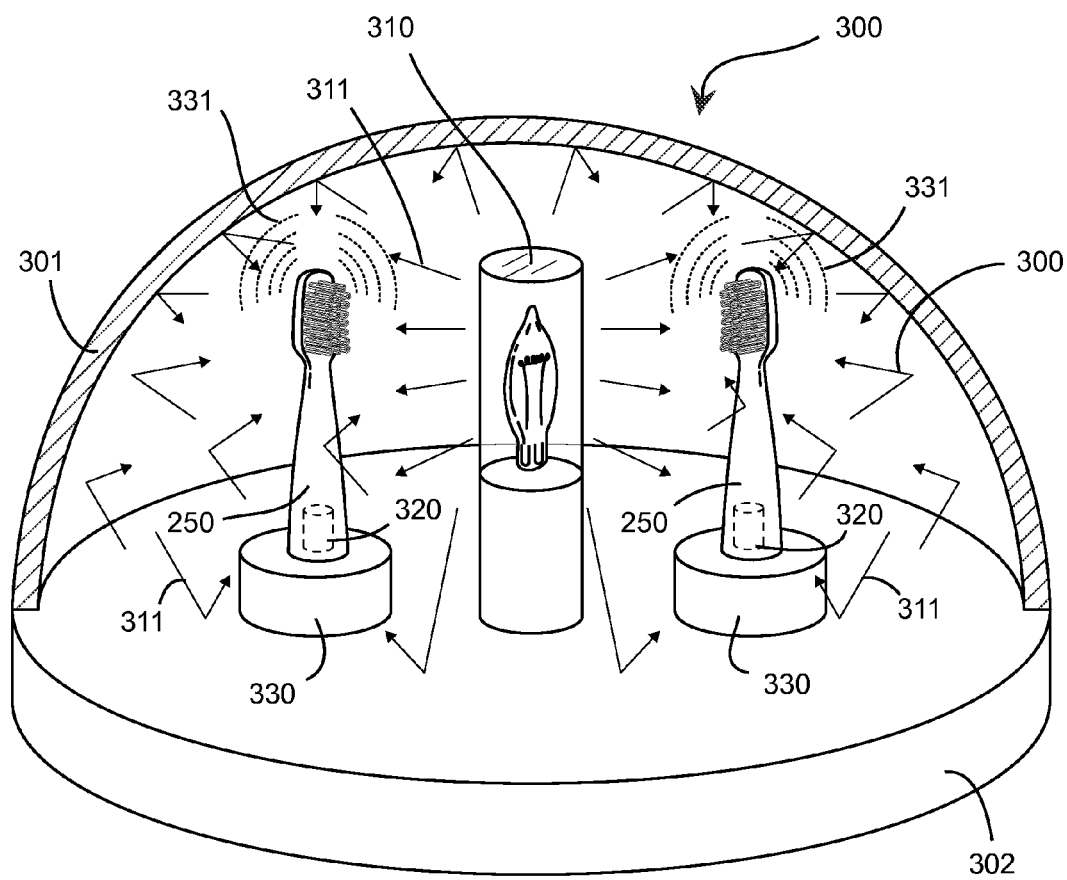
FIG. 15 shows an external sanitization device having a plurality of dental accessory engagement members, each of the engagement members being configured to communicate ultrasonic energy or vibrations to a head portion of an attached dental accessory, and the sanitization device is further configured to communicate ultraviolet light within the sanitation chamber volume of the sanitization device.

FIG. 15 shows an external sanitization device having a plurality of dental accessory attachment members, each of the attachment members being configured to communicate ultrasonic energy or vibrations to a head portion of an attached dental accessory, and the sanitization device is further configured to communicate ultraviolet light within the sanitation chamber volume of the sanitization device.

In FIG. 15, the sanitization device 300 comprises a base 302 and a cover 301 mated therewith. The cover 301 comprises a top portion at an apex of the illustrated dome shape cover, and a side wall forming the vertical portion of the dome shape. The side wall extends to mate with a periphery of the base 302. A volume between the cover 301 and the base 302 defines a sanitation chamber, wherein one or more dental accessories may become sterilized using one or more of ultraviolet light radiation and/or ultrasonic energy. The device comprises a pair of attachment members 330 positioned at the base and configured to engage a notch 320 of a respective dental accessory 250. Each of the attachment members is configured to communicate vibrations 331 from an ultrasonic sound frequency generator to an engaged dental accessory, and particularly a head portion thereof. One or more ultrasonic sound frequency generators can be provided, with the one or more generators individually or collectively coupled to each of the respective attachment members of the device. In addition, the device comprises an ultraviolet light emitting source 310, such as a UV light bulb or similar means, the source being positioned about the base of the device. The ultraviolet light emitting source is configured to communicate ultraviolet light 311 therefrom. The dome is shown comprising a reflective surface for reflecting the ultraviolet light 311 for reuse within the sanitization chamber.

Figure 16:
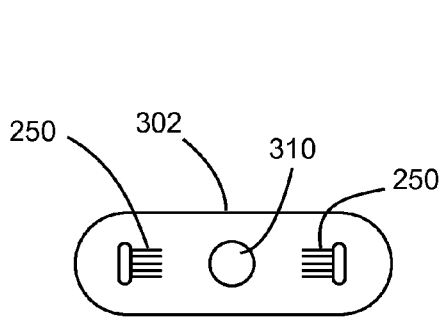
FIG. 16 shows a top view of an external sanitization device in accordance with the embodiments herein, the device being configured for sterilizing two dental accessories, wherein each of the two dental accessories are positioned adjacent to an ultraviolet light emitting source, and a useable side of each dental accessory is further configured to face the ultraviolet light source for sanitizing.

FIG. 16 shows a top view of an external sanitization device in accordance with the embodiments herein, the device being configured for sterilizing two dental accessories 250, wherein each of the two dental accessories 250 are positioned adjacent to an ultraviolet light emitting source 310, and a useable side of each dental accessory is further configured to face the ultraviolet light source for sanitizing. In this embodiment the base 302 may have an oblong shape, or having a length longer than its width.

Figure 17:
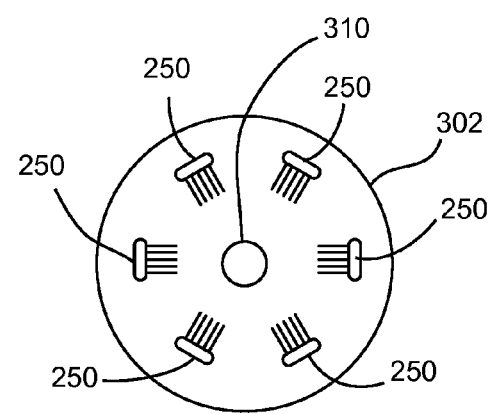
FIG. 17 shows a top view of an external sanitization device in accordance with the embodiments herein, the device being configured for sterilizing a plurality of dental accessories, wherein each of the plurality of dental accessories is positioned adjacent to an ultraviolet light emitting source, and a useable side of each dental accessory is further configured to face the ultraviolet light source for sterilizing.

FIG. 17 shows a top view of an external sanitization device in accordance with the embodiments herein, the device being configured for sterilizing a plurality of dental accessories 250, wherein each of the plurality of dental accessories 250 is positioned adjacent to an ultraviolet light emitting source 310, and a useable side of each dental accessory is further configured to face the ultraviolet light source for sterilizing. In this embodiment the base 302 may have a circular shape.

Figure 18:
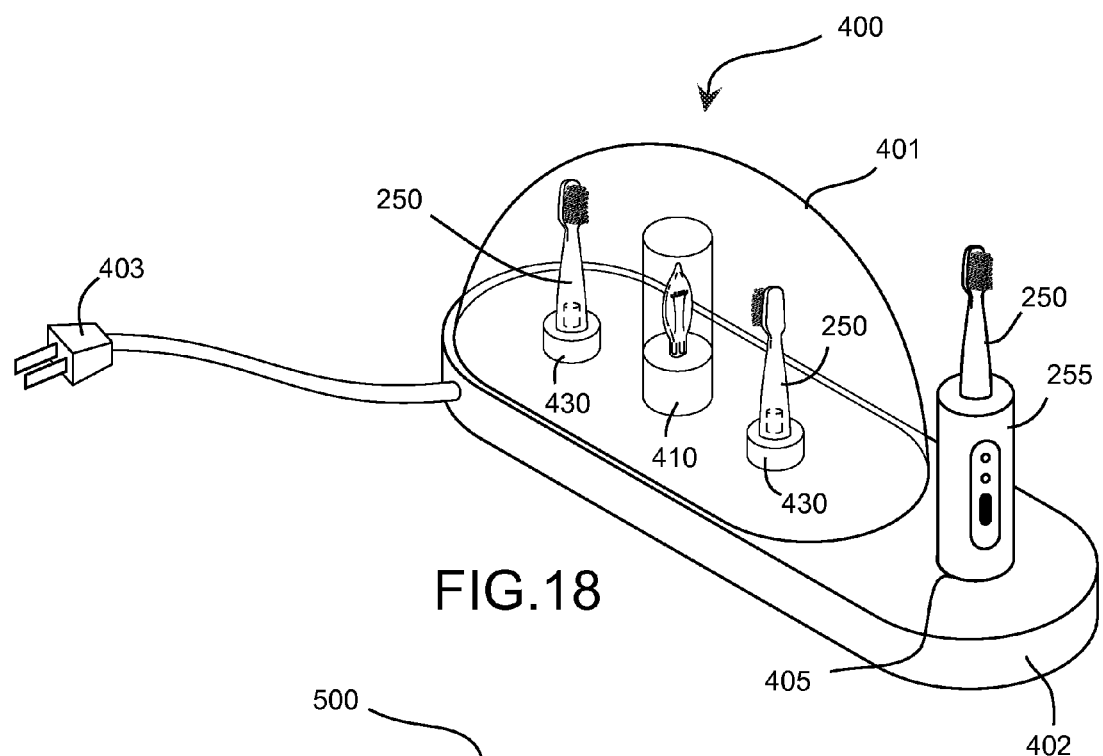
FIG. 18 shows an external sanitization device in accordance with the embodiments herein, the device further includes a charging station and associated docking port for receiving and charging a powered dental instrument.

FIG. 18 shows an external sanitization device 400 in accordance with the embodiments herein, the device further includes a charging station and associated docking port 405 for receiving and charging a powered dental instrument 255. The device can comprise any style of power cord or battery source for power, however the illustrated embodiment is depicted with a standard plug adapter 403.

The device generally comprises a base 402 and a cover 401 coupled therewith, an area between the cover and the base defining a sanitation chamber. The device further comprises two attachment members 430, wherein each attachment member 430 is configured to engage a respective dental accessory 250 and maintain such in an upright position such that a useable portion of the accessory is oriented to face an ultraviolet light emitting source 410, such as an ultraviolet light. Although the accessory is being shown oriented upright with respect to the base, it should be recognized that the accessory can be oriented sideways, or at any angle, but ideally such that the accessory is positioned in a manner for sterilization of the useable portion, for example the bristles of a tooth brush accessory should be oriented to face the UV light source.

Although the cover 401 of the device is shown as a transparent cover it should be appreciated that a reflective cover may be provided for reusing or containing the ultraviolet light within the sanitation chamber of the device.

Although not illustrated in this figure, the device may comprise one or more ultrasonic sound frequency generators for communicating ultrasonic energy to the one or more contained dental accessories. As above, one or more of the attachment members can be coupled to the ultrasonic sound frequency generators, either independently or collectively.

Figure 19:
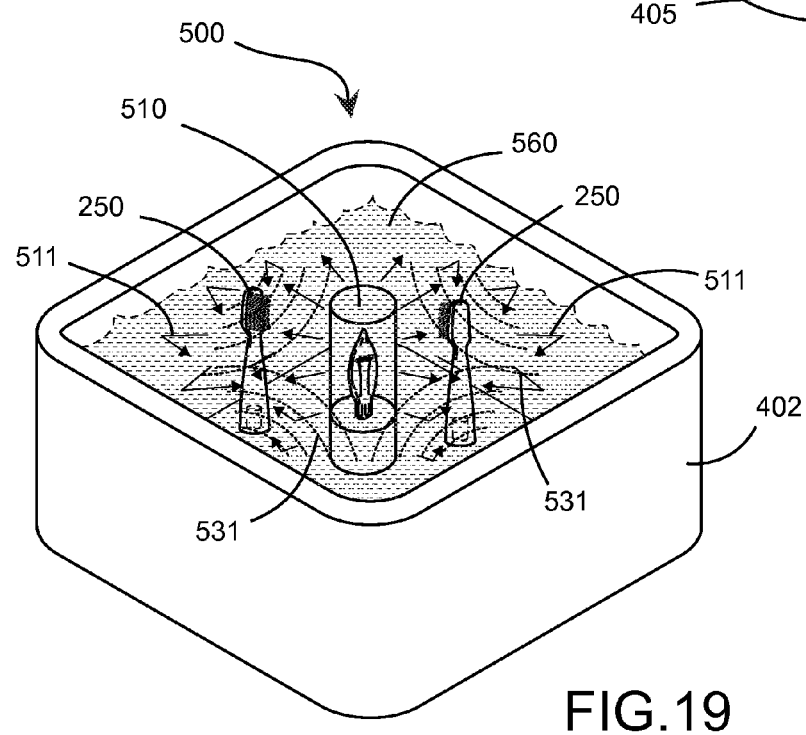
FIG. 19 shows an external sanitization device in accordance with the embodiments herein, the device comprises an ultraviolet light emitting source and a bath containing a liquid for communicating ultrasonic energy to one or more dental accessories being sterilized therein.

FIG. 19 shows an external sanitization device 500 in accordance with another embodiment, the device comprises an ultraviolet light emitting source 510 and a bath containing a liquid 560 for communicating ultrasonic energy 531 from an ultrasonic sound frequency generator (not shown) to one or more dental accessories 250 being sterilized therein. The ultraviolet light emitting source 510 is shown emitting ultraviolet light 511 which is communicated through the bath. The liquid may comprise water, alcohol, or other liquid suitable for communicating ultrasonic sound waves 531 and ultraviolet light 511.

Figure 20:
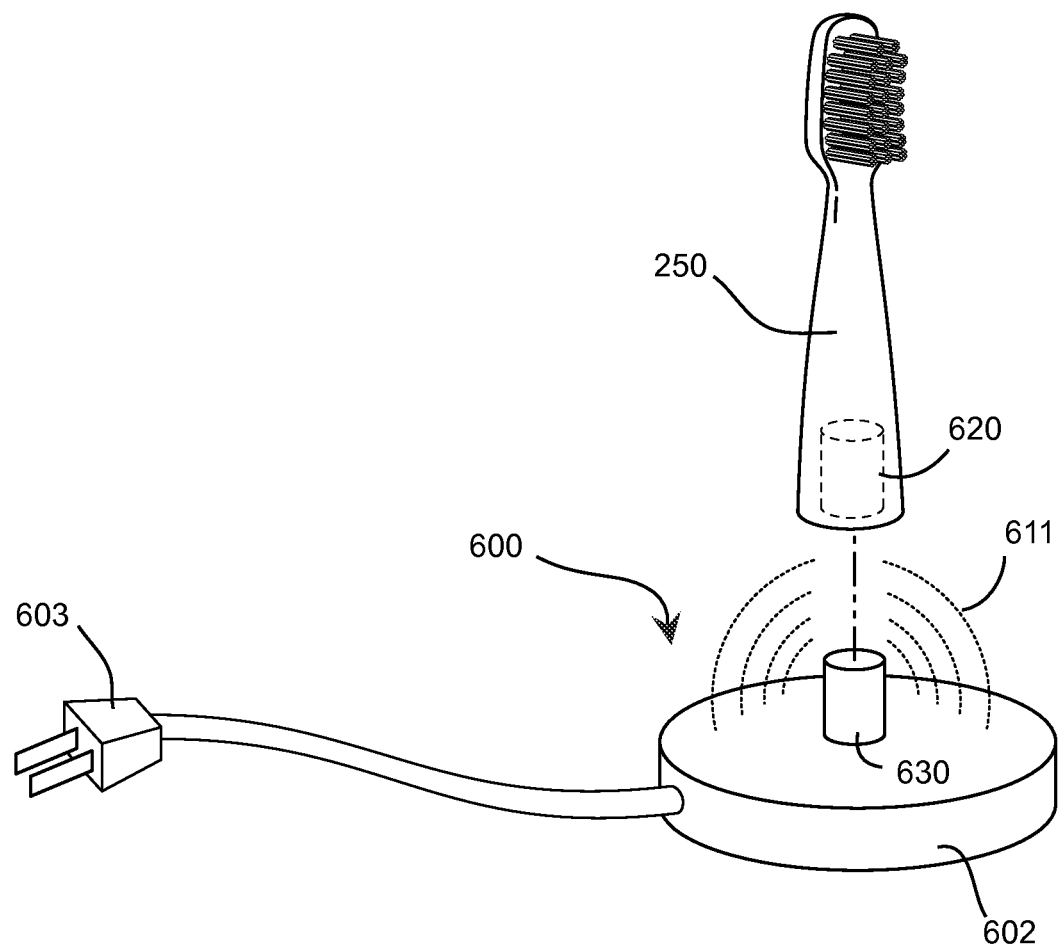
FIG. 20 shows a sanitization device configured to receive a dental accessory at a base portion of the device, and further configured to communicate ultrasonic energy from the base to a head portion of the dental accessory.

FIG. 20 shows a sanitization device 600 configured to receive a dental accessory 250 at a base portion 602 of the device, and further configured to communicate ultrasonic energy 611 from the base to a head portion of the dental accessory. In this embodiment, an attachment member 630 is coupled to the base 602, and the ultrasonic energy source is housed within the base and coupled to the attachment member 630 such that when the accessory 250 is engaged with the attachment member, the resulting ultrasonic energy 611 is communicated from the base to the accessory, and particularly to a head portion of the accessory such as the bristles of a toothbrush as shown.

FIG. 21A shows a base 602 with an attachment member 630 disposed thereon, the attachment member is configured to engage a toothbrush device with a built in sanitization chamber. Moreover, the base comprises at least one ultrasonic generator, the generator capable of communicating ultrasonic energy through the attachment member to the engaged toothbrush device. In a preferred embodiment, the ultrasonic generator is configured to communicate ultrasonic energy through the attachment member and to the toothbrush accessory 250 within the sanitization chamber housing 111 of the dental device.

FIG. 21B is similar to the embodiment of FIG. 21A; however, FIG. 21B shows an external sanitization device 200A being coupled to the base 602 such that an ultrasonic frequency generator within the base is configured to communicate ultrasonic energy into the external sanitization device 200A through an attachment member 630. In particular, a dental accessory 250 is shown having a notch 220 configured to engage with the attachment member 630.

Thus, in various embodiments, a sanitization device for dental accessories is provided which utilizes one or more of ultrasonic sound energy, or ultraviolet light, for sanitizing. Although preferred embodiments are illustrated, it will be recognized by those having skill in the art that certain variations of the disclosed features and functions described herein can be implemented in various alternative embodiments which achieve substantially similar results. Accordingly, the descriptions and embodiments herein should not be considered as limiting the invention as claimed.

Moreover, the various components of the device disclosed herein can be formed of conventional materials such as plastic or metal, however, can be formed of any material suitable for the purposes set forth in this disclosure.

This invention has other applications, potentially, and one skilled in the art could discover these. The explication of the features of this invention does not limit the claims of this application; other applications developed by those skilled in the art will be included in this invention.

It is additionally noted and anticipated that although the device is shown in its most simple form, various components and aspects of the device may be differently shaped or slightly modified when forming the invention herein. As such those skilled in the art will appreciate the descriptions and depictions set forth in this disclosure or merely meant to portray examples of preferred modes within the overall scope and intent of the invention, and are not to be considered limiting in any manner.

While all of the fundamental characteristics and features of the invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

We claim:

1. A sanitization device configured for sterilization of one or more dental accessories, the sanitization device comprising:
    a base having one or more attachment members, each of said attachment members being configured to engage with one of said dental accessories for maintaining an orientation thereof about the base;
    a cover having a top portion and one or more side walls extending therefrom, wherein said side walls are configured to engage a periphery of the base and form an engagement therebetween; said cover when coupled to the base in a closed-position forming an interior volume therebetween defining a sanitation chamber; and each of;
- at least one ultraviolet light emitting source disposed within the sanitation chamber; and
- at least one ultrasonic sound frequency generator configured to communicate ultrasonic energy within the sanitation chamber;

wherein said attachment member is coupled to said ultrasonic sound frequency generator.

2. The sanitation device of claim 1, wherein said ultrasonic sound frequency generator is one of: an ultrasonic transducer or an ultrasonic motor.

3. A sanitization device configured for sterilization of one or more dental accessories, the sanitization device comprising:
- a base having one or more attachment members, each of said attachment members being configured to engage with one of said dental accessories for maintaining an orientation thereof about the base;
- a cover having a top portion and one or more side walls extending therefrom, wherein said side walls are configured to engage a periphery of the base and form an engagement therebetween; said cover when coupled to the base in a closed-position forming an interior volume therebetween defining a sanitation chamber; and one or more of;
- at least one ultraviolet light emitting source disposed within the sanitation chamber; and
- at least one ultrasonic sound frequency generator configured to communicate ultrasonic energy within the sanitation chamber; or a combination thereof;

wherein said attachment member is coupled to said ultrasonic sound frequency generator.

4. The sanitization device of claim 3, said device comprising:
- at least one ultraviolet light emitting source disposed within the sanitation chamber; and
- at least one ultrasonic sound frequency generator configured to communicate ultrasonic energy within the sanitation chamber.

5. The sanitization device of claim 3, wherein at least one of said attachment members is configured to communicate said ultrasonic energy to a dental accessory engaged therewith.

6. The sanitization device of claim 3, wherein said ultrasonic sound frequency generator is coupled to said base.

7. The sanitization device of claim 3, wherein said ultrasonic sound frequency generator is coupled to said cover.

8. The sanitization device of claim 3, wherein said ultrasonic sound frequency generator is configured to communicate sound within the sanitation chamber at a frequency between 20 KHz and 100 KHz.

9. The sanitization device of claim 3, wherein each of said dental accessories is one of: a toothbrush, flosser, pic, massager, tongue cleaner, or a combination thereof.

10. The sanitization device of claim 3, said device comprising:
- an ultraviolet light emitting source disposed about said base, and
- further comprising two attachment members disposed at said base, each of said attachment members being configured to engage with one of said dental accessories for maintaining an orientation thereof about the base;
- wherein a first of said two attachment members is disposed adjacent to said ultraviolet light emitting source and positioned at a first side thereof; and
- wherein a second of said two attachment members is disposed adjacent to said ultraviolet light emitting source and positioned at a second side thereof opposite of the first side.

11. The sanitization device of claim 10, wherein each of said attachment members is configured to orient the respective dental accessory engaged therewith such that a head portion of the engaged dental accessory is configured to face the ultraviolet light emitting source.

12. The sanitization device of claim 3, said device comprising:
- an ultraviolet light emitting source disposed about said base, and
- further comprising three or more attachment members disposed at said base, each of said attachment members being configured to engage with one of said dental accessories for maintaining an orientation thereof about the base;
- wherein each of said attachment members is disposed adjacent to said ultraviolet light emitting source and positioned radially therefrom.

13. The sanitization device of claim 12, wherein each of said attachment members is configured to orient the respective dental accessory engaged therewith such that a head portion of the engaged dental accessory is configured to face the ultraviolet light emitting source.

14. The sanitization device of claim 3, wherein said cover is transparent.

15. The sanitization device of claim 3, wherein said cover is configured to reflect ultraviolet light emitted from the ultraviolet light emitting source such that said ultraviolet light is configured for reuse within the sanitation chamber.

16. The sanitization device of claim 3, wherein said cover further comprises a reflective surface for reflecting ultraviolet light within the sanitation chamber.

17. The sanitization device of claim 3, wherein said base is configured to form a bath containing a liquid therein, wherein said base is configured to communicate said ultrasonic energy through said liquid therein.

18. The sanitization device of claim 3, further comprising a charging station and associated docking port for receiving and charging a powered dental instrument.

19. The sanitization device of claim 3, said cover forming a portion of an external sanitization chamber; wherein said external sanitization chamber is adapted to couple with the base for communicating the ultrasonic energy from the base to an accessory within the sanitation chamber.

* * * * *